US009155722B2

(12) United States Patent
Fowers et al.

(10) Patent No.: US 9,155,722 B2
(45) Date of Patent: Oct. 13, 2015

(54) RECONSTITUTABLE REVERSE THERMAL GELLING POLYMERS

(75) Inventors: Kirk D. Fowers, Centerville, UT (US); Ramesh C. Rathi, Cottonwood Heights, UT (US); Ai-Zhi Piao, Salt Lake City, UT (US)

(73) Assignee: PROTHERICS SALT LAKE CITY, INC., Salt Lake City, UT (US)

( * ) Notice: Subject to any disclaimer, the term of this patent is extended or adjusted under 35 U.S.C. 154(b) by 0 days.

(21) Appl. No.: 12/886,387

(22) Filed: Sep. 20, 2010

(65) Prior Publication Data

US 2011/0071216 A1    Mar. 24, 2011

Related U.S. Application Data

(63) Continuation of application No. 12/562,653, filed on Sep. 18, 2009.

(60) Provisional application No. 61/275,717, filed on Sep. 18, 2009.

(51) Int. Cl.
*A61K 31/337* (2006.01)
*A61K 9/14* (2006.01)
*A61K 47/14* (2006.01)

(52) U.S. Cl.
CPC .................................... *A61K 31/337* (2013.01)

(58) Field of Classification Search
USPC ......................................................... 424/489
See application file for complete search history.

(56) References Cited

U.S. PATENT DOCUMENTS

| | | | |
|---|---|---|---|
| 5,702,717 | A | 12/1997 | Cha et al. |
| 6,004,573 | A | 12/1999 | Rathi et al. |
| 6,117,949 | A | 9/2000 | Rathi et al. |
| 6,201,072 | B1 | 3/2001 | Rathi et al. |
| 6,592,899 | B2 | 7/2003 | Fowers et al. |
| 7,018,645 | B1 | 3/2006 | Piao et al. |
| 7,135,190 | B2 | 11/2006 | Piao et al. |
| 2003/0082234 | A1 | 5/2003 | Seo et al. |
| 2004/0001872 | A1* | 1/2004 | Shih et al. ............. 424/426 |
| 2004/0185101 | A1 | 9/2004 | Shih et al. |
| 2006/0041102 | A1 | 2/2006 | Hossainy et al. |
| 2007/0003592 | A1 | 1/2007 | Hissink |
| 2007/0031499 | A1 | 2/2007 | Huh et al. |
| 2007/0155906 | A1 | 7/2007 | Hissink et al. |
| 2007/0244259 | A1 | 10/2007 | Lee et al. |
| 2008/0247987 | A1 | 10/2008 | Liggins et al. |
| 2009/0285873 | A1 | 11/2009 | Lim et al. |

FOREIGN PATENT DOCUMENTS

| | | |
|---|---|---|
| CN | 1916050 | 2/2007 |
| CN | 1958074 | 5/2007 |

OTHER PUBLICATIONS

Lee et al., "Thermoreversible gelation of biodegradable poly(e-caprolactone) and poly(ethylene glycol) multiblock copolymers in aqueous solutions", 2001, Journal of Controlled Release, vol. 73, pp. 315-327.*
International Search Report and Written Opinion for International Application No. PCT/US2010/049526, mailed Nov. 3, 2010.
Bae et al., "Thermogelling Poly(caprolactone-b-ethylene glycon-bcaprolactone) Aqueous Solutions," Macromolecules, vol. 38, pp. 5260-5265 (2005).
Lee et al., Thermoreversible Gelation of Biodegradable Poly(ε-caprolactone) and Poly(ethylene glycol) Multiblock Copolymers in Aqueous Solutions, Journal of Controlled Release, vol. 73, pp. 315-327 (2001).
Jiang, et al. (2007) "Injectable Hydrogels of Poly(E-caprolactone-co-glycolide)-poly (ethylene glycol)-poly(E-Caprolactone-co-glycolide) Triblock Copolymer Aqueous Solutions," Science Direct, Polymer 48: 4786-4792.
Jiang, et al. (2007) "Thermogelling Hydrogels of Poly(E-Caprolactone-co-D,L-lactide)-Poly(Elhylene glycol)-Poly(E-caprolactone-co-D, L-lactide) and Poly(E-Caprolactone-co-L-lactide)-Poly(ethylene glycol)-Poly(E-Caprolactone-co-L-lactidel Aaueous Solutions," Wiley InterScience, 45: 4091-4099.
Yu, et al. (2008) Injectable Hydrogels as Unique Biomedical Material, Chemical Society Review 37: 1473-1481.
He, et al. (2008) "In Situ Gelling Stimuli-Sensitive Block Copolymer Hydrogels for Drug Delivery" Journal of Controlled Release 127: 189-207.
Hwang, et al. (2005) "Caprolaclonic Poloxamer Analog: PEG-PCL-PEG" Biomacromolecules 6: 885-890.
Jeong, et al. (2002) "Thermosensitive Sol-Gel Reversible Hydrogels," Advanced Drug Delivery Reviews 54: 37-53.
Jeong, et al. (1997) "Biodegradable Block Copolymers as Injectable Drug-Delivery Systems", Nature 388: 860-862.
Jiang, et al. (2008) Biodegradable and Thermoreversible hydrogels of Poly(ethylene glycol)-Poly(E-Caprolactone-Co-Glycolide)-Poly(Ehtylene Glycol) Aqueous Solutions, Wiley InterScience. 87A: 45-51.
Jiang, et al. (2008) "Effect of Microstructures on the Phase Transition Behavior of P(CL-GL)-PEG-P(CL-GL) Triblock Copolymer Aqueous Solutions," Wiley InterScience, 29: 1264-1268.

* cited by examiner

*Primary Examiner* — Michael B Pallay
(74) *Attorney, Agent, or Firm* — Hunton & Williams LLP (57) ABSTRACT

Biodegradable and bioabsorbable block copolymers, which can be in the form of solid powder or powder wax compositions that can be easily reconstituted into an aqueous polymer solution and exhibit reverse thermal gellation properties upon exposure to elevated temperatures, are provided. Methods of making using these copolymers are also provided.

44 Claims, 4 Drawing Sheets

RECONSTITUTABLE REVERSE THERMAL GELLING POLYMERS

The subject application claims benefit of Provisional Application No. 61/275,717 filed Sep. 18, 2009, which was converted from application Ser. No. 12/562,653 filed Sep. 18, 2009.

BACKGROUND OF THE INVENTION (a) Field of the Invention

The present invention relates to biodegradable and bioabsorbable block copolymers in solid powder or powder wax form that can be easily formed into an aqueous polymer solution and exhibit reverse thermal gellation properties upon exposure to elevated temperatures, such as upon exposure to body temperature just prior to or upon administration. The disclosed polymers are advantageously used, for example, in the parenteral administration of drugs.

(b) Description of the Related Art

Biodegradable block copolymers exhibiting reverse thermal gellation are disclosed in U.S. Pat. Nos. 6,201,072; 6,117,949; and 6,004,573 to Rathi et al. and U.S. Pat. No. 5,702,717 to Cha et al. These polymer compositions exist as a liquid solution at low temperatures, then reversibly form gels at physiologically relevant temperatures, and provide good drug release characteristics. These compositions include biodegradable ABA- or BAB-type block copolymers having an average molecular weight of between about 2000 and 4990, and include about 51 to 83% by weight of an hydrophobic A polymer block comprising a biodegradable polyester and about 17 to 49% by weight of a hydrophilic B polymer block comprised of polyethylene glycol. U.S. Pat. Nos. 7,018,645 and 7,135,190 to Piao et al., disclose mixtures of triblock copolymers exhibiting similar reverse thermal gellation properties.

These polymeric drug delivery polymers exhibit reverse thermal gellation properties, but have been found to be especially difficult to form or reconstitute into aqueous drug delivery compositions. The difficulty in reconstituting these compositions has necessitated performing the reconstitution step in a manufacturing facility to produce an aqueous drug delivery product. After reconstitution, these aqueous drug delivery products exhibiting reverse thermal gellation would typically be stored in the form of frozen aqueous polymer solution up to the point of use. At room temperature, aqueous polymer solutions of these reverse thermal gellation polymers would begin to degrade. Therefore, these aqueous drug delivery compositions would need to be shipped and stored in a refrigerated or frozen state. Previously known reverse thermal gellation drug delivery compositions, such as those disclosed by Rathi et al., exhibit good stability if stored and shipped in frozen form. For drug delivery applications, the polymers disclosed by Rathi et al. can be stored and shipped in ready-to-inject prefilled syringes or product vial configurations (single or double vial). The syringes and vials are thawed prior to injection, which takes between 24 and 48 hours.

Other ABA triblock copolymers have incorporated caprolactone and glycolic acid into the hydrophobic blocks with a single hydrophilic polymers. See Chinese Published Application No. CN 1958074 A. However, the synthetic methods disclosed therein are inadequate to produce a triblock copolymer composition having a desirable molecular weight and polymer properties. For example, the synthetic methods disclosed therein rely on the use of a commercially available polyethylene glycol monomer of a nominal molecular weight (i.e., 1540 Daltons). Although polyethylene glycol having specific nominal molecular weights other than 1540 are available, it has been found that triblocks made from a single polyethylene glycol component with a single average molecular weight lack the most desirable combination of reconstitution, drug release, swelling and dissolution characteristics for the range of drugs utilized and in the indications essential for controlled release systems.

The present inventors have found that the drug release, degradation, swelling and dissolution characteristics depend significantly on the composition of the thermoreversible block copolymer. Specifically, it has been found that precise control of the hydrophilic polymer length as well as the hydrophobic polymer composition is critical to obtaining a desirable reconstitution, drug release, swelling and dissolution characteristics. Prior block copolymers exhibiting reverse thermal gellation properties have been found to have inadequate reconstitution, drug release, swelling, and/or dissolution characteristics. Accordingly, there is a need in the art for an aqueous biodegradable polymeric drug delivery composition exhibiting reverse thermal gellation that can be stored at room temperature and easily formed or reconstituted at the point of use in a minimal amount of time having desirable drug release, swelling and dissolution characteristics.

SUMMARY OF THE PREFERRED EMBODIMENTS

Novel reconstitutable block copolymers in solid powder or powder wax form having thermally reversible gelation properties upon reconstitution have been developed. The non-aqueous solid powder or powder wax form of the polymers provides enhanced stability relative to prior art compositions and do not require freezing and/or refrigeration. This stability allows for storage at room temperature which advantageously eliminates the need for refrigeration from the point of manufacture until the product is used. The reconstitutable polymers of the present invention provide improved handling and compatibility with unstable and sensitive drugs.

The reconstitutable polymers can be prepared in aqueous form at the point of use and do not require additives or application of heat in excess of 60° C. to prepare in aqueous form. For example, the reconstitutable polymers can be put into aqueous form suitable for parenteral or intratumoral administration at the point of use by a physician. The polymers can be reconstituted at the point of use by agitation, e.g., stirring and/or vortexing, the polymer in combination with water or buffer with mild heating (i.e., below 60° C.). If desired, a drug can be incorporated into the drug delivery composition before, during, or after reconstitution. Further, the drug can be incorporated as part of the dry powder composition.

The unique synthetic methods disclosed herein allow precise control of the polymer physico-chemical properties, such as the gelation temperature. For example, the gelation temperature of the reconstituted polymer can be precisely controlled within the range of 26 to 35° C. Such polymer may be formulated to have desirable swelling and drug release characteristics. For example, if desired, the polymer may exhibit less than 5% swelling after 30 days of aqueous exposure, and release between about 10 to 15% of paclitaxel in five days and 15% to 20% of paclitaxel in 20 days. Whereas prior synthetic methods relied on the use of a single commercially available hydrophilic polymer as a building block of the block copolymers, certain embodiments of the present invention achieve superior polymers using novel synthetic methods. As described in further detail below, these novel methods include the use of two or more hydrophilic polymers in the formation of block copolymers. The inventors have discovered that superior reconstitution, release, degradation, swelling and/or dissolution characteristics can be achieved when two hydrophilic polymer precursors which have different average molecular weights are used in the reaction. For instance, a first poly ethylene glycol polymer composition having a nominal molecular weight of 1000 Daltons and a second poly ethylene glycol polymer composition having a nominal molecular weight of 1450 Daltons can be used together in a variety of ratios in the reaction with biodegradable polyester forming monomers. Other combinations of hydrophilic polymer precursors are contemplated. As shown in the attached figures, such unique synthetic methods are capable of making a biodegradable polymeric drug delivery compositions exhibiting reverse thermal gellation that can be stored at room temperature and easily formed or reconstituted at the point of use in a minimal amount of time having desirable drug release, swelling and dissolution characteristics.

The reconstitutable polymers of the present invention can be injected at room temperature allowing for versatile use in either hospitals, clinics, or for in-home use. The reconstitutable polymers can be subject to gamma sterilization without adverse effects resulting from degradation or free radical reactions. The product can also be supplied conveniently in two or three vial product configurations depending on the application. It is an object of the present invention to provide low molecular weight block copolymer drug delivery systems that are distributed in a stable solid form, yet form biodegradable, bioabsorbable polymer solutions at room temperature. The polymer solutions exhibit reverse thermal gelation behavior, namely, exist as a liquid solution at low temperatures, reversibly form gels at physiologically relevant temperatures, and provide good drug release characteristics. The polymers of the present invention can have a gel temperature which is below or at body temperature such that a gel is formed upon injection, or the polymer may be adapted to form a gel prior to administration.

A further object of this invention is to provide a drug delivery system for the parenteral or intratumoral administration of hydrophilic and hydrophobic drugs, peptide and protein drugs, hormones, genes/nucleic acids, oligonucleotides and anti-cancer agents. Classes of anti-cancer agents include, for example, alkylating agents, antimetabolites, antibiotics, hormonal agents, anti-vascularization or nitrosureas.

These and other objects are accomplished by means of an AB-, ABA-, or BAB-block copolymer composition, the block copolymer comprising at least a first AB, ABA, or BAB block copolymer component comprising a first hydrophobic A-block and a first hydrophilic B-block, wherein the first hydrophobic A-block is a biodegradable polyester comprising at least 60% caprolactone and at least one second polyester-forming monomer, and the first hydrophilic B-block has a first average molecular weight and comprises polyethylene glycol; at least a second AB, ABA, or BAB block copolymer component comprising a second hydrophobic A-block and a second hydrophilic B-block, wherein the second hydrophobic A-block comprises biodegradable polyester, and the second hydrophilic B-block has a second average molecular weight and comprises polyethylene glycol, wherein the second average molecular weight is different from the first average molecular weight; wherein the block copolymer composition has a total average molecular weight from 1500 to 10,000 Daltons, a total A-block content of the composition is from about 60 to 85% by weight, and a total B-block content of the composition is from about 15% to 40% by weight, wherein the total average molecular weight of the B-block in the composition is from 300 to 2000 Daltons, wherein the block copolymer composition is a powder or wax at room temperature, is capable of exhibiting reverse thermal gellation when formed as an aqueous polymer solution, and is capable of being converted into an aqueous polymer solution in less than thirty minutes by agitating without the use of additives or heat exceeding 60° C.

This invention also include novel forms of administration of at least one drug to a warm blooded animal in a controlled release form. These novel methods comprise (1) providing an AB-, ABA-, or BAB-block copolymer composition, which is a powder or wax at room temperature, is capable of exhibiting reverse thermal gellation when formed as an aqueous polymer solution, and is capable of being converted into an aqueous polymer solution in less than thirty minutes by agitating without the use of additives or heat exceeding 60° C.; (2) forming an aqueous solution of said powder or wax composition by combining the copolymer with water without exposing to heat exceeding 60° C.; and (3) administering said composition to said warm blooded animal as a gel depot in the warm blooded animal.

The invention further involves methods of making powder or wax block copolymer compositions. These methods include (1) providing an ABA-block copolymer composition comprising: i) about 60 to 85% by weight of a biodegradable, hydrophobic A-block comprising a biodegradable polyester, wherein said A-block includes at least 60% caprolactone and at least one second polyester-forming monomer; and ii) about 15 to 40% by weight of a biodegradable, hydrophilic B-block comprising a polyethylene glycol, wherein the molecular weight of the B-block is between 300 and 2000 Daltons, (2) freeze drying said block copolymer to form the powder or wax block copolymer composition, wherein the powder or wax block copolymer composition is a solid at room temperature, is capable of exhibiting reverse thermal gellation when formed as an aqueous polymer solution, and is capable of being converted into an aqueous polymer solution in less than thirty minutes by agitating without the use of additives or heat exceeding 60° C.

These and other objects may be accomplished by means of an ABA-block copolymer, said block copolymer comprising: i) about 60 to 85% by weight of a biodegradable, hydrophobic A-block comprising a biodegradable polyester, wherein said A-block includes at least 85% caprolactone and at least one second polyester-forming monomer; and ii) about 15 to 40% by weight of a biodegradable, hydrophilic B-block comprising a polyethylene glycol, wherein the molecular weight of the B-block is between 1000 and 1450 Daltons; wherein the block copolymer composition is a powder or wax at room temperature, is capable of exhibiting reverse thermal gellation when formed as an aqueous polymer solution, and is capable of being converted into an aqueous polymer solution in less than thirty minutes by agitating without the use of additives or heat exceeding 60° C. More preferably, the ABA-block copolymer has an A-block content of the copolymer ranges that from 65 to 80% and a B-block content of the copolymer ranges from 20 to 35%, and most preferably, an A-block content that ranges from 67 to 75% and a B-block content that ranges from 25 to 33%. The second polyester monomer preferably comprises a residue of at least one of D,L-lactide, D-lactide, L-lactide, D,L-lactic acid, D-lactic acid, L-lactic acid, glycolide, glycolic acid, ε-hydroxy hexonoic acid, γ-butyrolactone, γ-hydroxy butyric acid, δ-valerolactone, δ-hydroxy valeric acid, hydrooxybutyric acids, malic acid, or copolymers thereof, and more preferably the second polyester monomer comprises residues from lactide or glycolide or copolymers thereof, and most preferably the second polyester monomer comprises residues from glycolide. Preferably, the A-block comprises at least 85% caprolactone, more preferably, the biodegradable polyester of the A-block comprises at least 90 mole % caprolactone, and most preferably, the biodegradable polyester of the A-block comprises approximately 90 to 95% caprolactone. Preferably, the ABA-block copolymer has an average molecular weight of the B-block from 800 to 1800 Daltons, more preferably, the average molecular weight of the B-block is from 1000 to 1600 Daltons, and most preferably, average molecular weight of the B-block is from 1200 to 1500 Daltons. Preferably, the block copolymer composition has a total average molecular weight from 4000 to 8000 Daltons, and more preferably, a total average molecular weight from 5500 to 7500 Daltons. The ABA-block copolymer is preferably a powder or wax composition that forms an aqueous polymer solution in less than 30 minutes without exposure to additional agents or temperatures exceeding 60° C., is capable of exhibiting less than 5% swelling after 30 days of aqueous exposure, and is capable of releasing between about 10 to 15% of paclitaxel in five days and 15% to 20% of paclitaxel in 20 days.

These and other objects may also be accomplished by means of an AB-block copolymer, said block copolymer comprising: i) about 60 to 85% by weight of a biodegradable, hydrophobic A-block comprising a biodegradable polyester, wherein said A-block includes at least 85% caprolactone and at least one second polyester-forming monomer; and ii) about 15 to 40% by weight of a biodegradable, hydrophilic B-block comprising a polyethylene glycol, wherein the molecular weight of the B-block is between 300 and 2000 Daltons; wherein the block copolymer composition is a powder or wax at room temperature, is capable of exhibiting reverse thermal gellation when formed as an aqueous polymer solution, and is capable of being converted into an aqueous polymer solution in less than thirty minutes by agitating without the use of additives or heat exceeding 60° C. More preferably, the AB-block copolymer has an A-block content of the copolymer ranges that from 65 to 80% and a B-block content of the copolymer ranges from 20 to 35%, and most preferably, an A-block content that ranges from 67 to 75% and a B-block content that ranges from 25 to 33%. The second polyester monomer preferably comprises a residue of at least one of D,L-lactide, D-lactide, L-lactide, D,L-lactic acid, D-lactic acid, L-lactic acid, glycolide, glycolic acid, ε-hydroxy hexonoic acid, γ-butyrolactone, γ-hydroxy butyric acid, δ-valerolactone, δ-hydroxy valeric acid, hydrooxybutyric acids, malic acid, or copolymers thereof, and more preferably the second polyester monomer comprises residues from lactide or glycolide or copolymers thereof, and most preferably the second polyester monomer comprises residues from glycolide. Preferably, the A-block comprises at least 85% caprolactone, more preferably, the biodegradable polyester of the A-block comprises at least 90 mole % caprolactone, and most preferably, the biodegradable polyester of the A-block comprises approximately 90 to 95% caprolactone. The AB-block copolymer preferably has an average molecular weight of the B-block from 300 to 800 Daltons, more preferably, the average molecular weight of the B-block is from 500 to 750 Daltons. Preferably, the block copolymer composition has a total average molecular weight from 1500 to 4500 Daltons, and more preferably, a total average molecular weight from 2000 to 4000 Daltons. The AB-block copolymer is preferably a powder or wax composition that forms an aqueous polymer solution in less than 30 minutes without exposure to additional agents or temperatures exceeding 60° C., is capable of exhibiting less than 5% swelling after 30 days of aqueous exposure, and is capable of releasing between about 10 to 15% of paclitaxel in five days and 15% to 20% of paclitaxel in 20 days.

These and other objects may be accomplished by means of a BAB-block copolymer, said block copolymer comprising: i) about 60 to 85% by weight of a biodegradable, hydrophobic A-block comprising a biodegradable polyester, wherein said A-block includes at least 85% caprolactone and at least one second polyester-forming monomer; and ii) about 15 to 40% by weight of a biodegradable, hydrophilic B-block comprising a polyethylene glycol, wherein the molecular weight of the B-block is between 300 and 2000 Daltons; wherein the block copolymer composition is a powder or wax at room temperature, is capable of exhibiting reverse thermal gellation when formed as an aqueous polymer solution, and is capable of being converted into an aqueous polymer solution in less than thirty minutes by agitating without the use of additives or heat exceeding 60° C. More preferably, the BAB-block copolymer has an A-block content of the copolymer ranges that from 65 to 80% and a B-block content of the copolymer ranges from 20 to 35%, and most preferably, an A-block content that ranges from 67 to 75% and a B-block content that ranges from 25 to 33%. The second polyester monomer preferably comprises a residue of at least one of D,L-lactide, D-lactide, L-lactide, D,L-lactic acid, D-lactic acid, L-lactic acid, glycolide, glycolic acid, ε-hydroxy hexonoic acid, γ-butyrolactone, γ-hydroxy butyric acid, δ-valerolactone, δ-hydroxy valeric acid, hydrooxybutyric acids, malic acid, or copolymers thereof, and more preferably the second polyester monomer comprises residues from lactide or glycolide or copolymers thereof, and most preferably the second polyester monomer comprises residues from glycolide. Preferably, the A-block comprises at least 85% caprolactone, more preferably, the biodegradable polyester of the A-block comprises at least 90 mole % caprolactone, and most preferably, the biodegradable polyester of the A-block comprises approximately 90 to 95% caprolactone. The BAB-copolymer has a molecular preferably has an average molecular weight from 300 to 800 Daltons for each B-block in the BAB-copolymer, and more preferably, the average molecular weight from 500 to 750 Daltons for each B-block in the BAB-copolymer. Preferably, the BAB-block copolymer composition has a total average molecular weight from 4000 to 8000 Daltons, and more preferably, a total average molecular weight from 5500 to 7500 Daltons. The BAB-block copolymer is preferably a powder or wax composition that forms an aqueous polymer solution in less than 30 minutes without exposure to additional agents or temperatures exceeding 60° C., is capable of exhibiting less than 5% swelling after 30 days of aqueous exposure, and is capable of releasing between about 10 to 15% of paclitaxel in five days and 15% to 20% of paclitaxel in 20 days.

BRIEF DESCRIPTION OF THE DRAWINGS

The above and other objects, features and advantages of the invention will become apparent from the following detailed description and the accompanying drawings.

DETAILED DESCRIPTION OF THE PREFERRED EMBODIMENTS

Additional objects and advantages of this invention will become apparent from the following summary and detailed description of the various embodiments of this invention. As used herein, the following terms shall have the assigned meanings:

"Parenteral" shall include intramuscular, intraperitoneal, intra-abdominal, subcutaneous, intratumoral, intracranial (or into the resected tumor cavity), intraarticular, ocual, and, to the extent feasible, intravenous and intraarterial.

"Gelation temperature" means the temperature at which the biodegradable block copolymer undergoes reverse thermal gelation, i.e. the temperature below which the block copolymer is soluble in water and above which the block copolymer undergoes phase transition to increase in viscosity or to form a semi-solid gel.

The terms "gelation temperature" and "reverse thermal gelation temperature" or the like shall be used interchangeably in referring to the gelation temperature.

"Polymer solution," "aqueous solution" and the like, when used in reference to a biodegradable block copolymer contained in such solution, shall mean a water based solution having such block copolymer dissolved therein at a functional concentration, and maintained at a temperature below the gelation temperature of the block copolymer.

Polyethylene glycol (PEG) is also sometimes referred to as poly(ethylene oxide) (PEO) or poly(oxyethylene) and the terms can be used interchangeably for the purposes of this invention.

"Reverse thermal gelation" is the phenomena whereby a solution of a block copolymer spontaneously increases in viscosity, and in many instances transforms into a semisolid gel, as the temperature of the solution is increased above the gelation temperature of the copolymer. For the purposes of the invention, the term "gel" includes both the semisolid gel state and the high viscosity state that exists above the gelation temperature. When cooled below the gelation temperature, the gel spontaneously reverses to reform the lower viscosity solution. This cycling between the solution and the gel may be repeated ad infinitum because the solution/gel transition does not involve any change in the chemical composition of the polymer system. All interactions to create the gel are physical in nature and do not involve the formation or breaking of covalent bonds.

"Drug delivery liquid" or "drug delivery liquid having reverse thermal gelation properties" shall mean a polymer solution that contains drug (the drug per se can either be dissolved or colloidal) suitable for administration to a warm-blooded animal which forms a gelled drug depot when the temperature is raised to or above the gelation temperature of the block copolymer.

"Depot" means a drug delivery liquid following administration to a warm-blooded animal which has formed a gel upon the temperature being raised to or above the gelation temperature.

"Gel" means the semi-solid phase that spontaneously occurs as the temperature of the "polymer solution" or "drug delivery liquid" is raised to or above the gelation temperature of the block copolymer. In certain situations, the formed gel may loose or absorb water from the surrounding environment to become more compact or swollen, such gels also fall within the scope of the invention.

"Aqueous polymer composition" means either a drug delivery liquid or a gel comprised of the water phase having uniformly contained therein a drug and the biodegradable block copolymer. At temperatures below the gelation temperature the copolymer may be soluble in the water phase and the composition will be a solution. At temperatures at or above the gelation temperature the copolymer will solidify to form a gel with the water phase, and the composition will be a gel or semi-solid.

"Biodegradable" means that the block copolymer can chemically break down or degrade within the body to form nontoxic components. The rate of degradation can be the same or different from the rate of drug release.

"Drug" shall mean any organic or inorganic compound or substance having bioactivity and adapted or used for a therapeutic purpose. Proteins, hormones, anti-cancer agents, oligonucleotides, DNA, RNA and gene therapies are included under the broader definition of drug.

"Peptide," "polypeptide," "oligopeptide" and "protein" shall be used interchangeably when referring to peptide or protein drugs and shall not be limited as to any particular molecular weight, peptide sequence or length, field of bioactivity or therapeutic use unless specifically stated. Such therapeutic uses may include, for example, alkylating agents, antimetabolites, antibiotics, hormonal agents, anti-vascularization or nitrosureas.

"Polycaprolactone-co-(lactide-co-glycolide)" or "PCLGA" shall mean a copolymer derived from the condensation copolymerization of caproic acid, lactic acid and glycolic acid, or, by the ring opening polymerization of α-hydroxy acid precursors, such as caprolactone, lactide or glycolide. "Polycaprolactone-co-glycolide" or "PCGA" shall mean a copolymer derived from the condensation polymerization of caproic acid and glycolic acid, or, by the ring opening polymerization of α-hydroxy acid precursors, such as caprolactone or glycolide. The terms "caprolactone and caproic acid" are used interchangeably, "lactide" and "lactate or lactic acid" are used interchangeably and the terms "glycolide" and "glycolate or glycolic acid" are used interchangeably.

"Poly(lactide)" or "PLA" shall mean a polymer derived from the condensation of lactic acid or by the ring opening polymerization of lactide. The terms "lactide" and "lactate or lactic acid" are used interchangeably.

"Biodegradable polyesters" refer to any biodegradable polyesters, which are preferably synthesized from at least one of D,L-lactide, D-lactide, L-lactide, D,L-lactic acid, D-lactic acid, L-lactic acid, glycolide, glycolic acid, ε-caprolactone, ε-hydroxy hexonoic acid, γ-butyrolactone, γ-hydroxy butyric acid, δ-valerolactone, δ-hydroxy valeric acid, hydrooxybutyric acids, malic acid, or copolymers thereof.

"Reconstitutable" or "reconstitution" shall mean a solid polymer that can be readily converted to an aqueous polymer solution without the need to add other agents in a timeframe of less than thirty minutes. The terms "reconstitutable" or "reconstitution" do not imply that the polymer composition is the same both before and after existing in a solid polymer form, or that the polymer composition has the same properties both before and after existing in a solid polymer form. The terms "reconstitutable" or "reconstitution" include aqueous polymer solutions formed for the first time from solid powders, even where the solid powder did not previously exist as an aqueous polymer solution.

The inventors have found that certain AB, ABA, and BAB block copolymers when prepared according to the methods disclosed herein have uniquely advantageous properties of being reconstitutable and still exhibiting reverse thermal gellation properties. Prior reverse thermal gellation polymer solutions would only form under extreme conditions involving application of additives, excessive heat (>60 degrees Celsius) or prolonged agitation. These properties made prior compositions impractical for reconstitution into a polymer solution at the point of use. The prior compositions were therefore shipped in refrigerated or frozen form to avoid degradation before use by the end user. The polymers disclosed herein overcome some or all of these deficiencies by providing a solid powder or powder wax form reconstitutable AB, ABA, or BAB block copolymer.

The block copolymers disclosed herein have hydrophobic or "A" block segments and hydrophilic or "B" block segments. Generally the block copolymer will be an AB-, ABA- or BAB-type block copolymer. However, the block copolymer could also be a multiblock copolymer having repeating BA or AB units to make A(BA)n or B(AB)n copolymers where n is an integer of from 2 to 5.

The solid powder or powder wax block copolymers have been found to meet the criteria summarized in Table 1, namely having compositional make-up within the indicated ranges. For purposes of disclosing molecular weight parameters, all reported molecular weight values are based on measurements by NMR or GPC (gel permeation chromatography) analytical techniques. The reported weight average molecular weights and number average molecular weights were determined by GPC and NMR respectively. The reported caprolactone and lactide/glycolide ratios were calculated from NMR data. GPC analysis was performed on a combination of Phenogel, mixed bed, and Phenogel, 500 Angstrom columns calibrated with PEG standards using RI detection and tetrahydrofuran as the eluent. NMR spectra were taken in $CDCl_3$ on a Bruker 200 MHz instrument.

TABLE 1

| | |
|---|---|
| Total weight average molecular weight: | 1500-10000 (by GPC) |
| PEG content: | 15 to 40% by weight<br>Preferred 20-35% by weight<br>Most preferred 25-33% by weight |
| Total polyester content: | 60 to 85% by weight<br>Preferred 65-80% by weight<br>Most preferred 67-75% by weight |
| ε-caprolactone content: | Greater than 60 mole percent<br>Preferably greater than 85 mole percent<br>More Preferred about 90-95 mole percent |
| Lactide/Glycolate content: | 0 to 40 mole percent<br>Preferred 0-15 mole percent<br>More Preferred about 5-10 mole percent |
| Behavior: | Solid powder or powder wax that is reconstitutable into a polymer solution that is water soluble below the gelation temperature yet gels above the gelation temperature |

AB, ABA and BAB type block copolymers may be synthesized by ring opening polymerization, or condensation polymerization according to the general reaction schemes disclosed in U.S. Pat. Nos. 5,702,717; 6,004,573; 6,117,949 and 6,201,072, hereby fully incorporated by reference. For example, the B(PEG) blocks may be coupled to the A blocks (polyesters) by ester or urethane links and the like. Condensation polymerization and ring opening polymerization procedures may be utilized as may the coupling of a monofunctional hydrophilic B block to either end of a difunctional hydrophobic A block in the presence of coupling agents such as isocyanates. Furthermore, coupling reactions may follow activation of functional groups with activating agents such as carbonyl diimidazole, succinic anhydride, N-Hydroxy succinimide and p-nitrophenyl chloroformate and the like.

The hydrophilic B-block is formed from PEG of appropriate molecular weights. PEG was chosen as the hydrophilic, water-soluble block because of its unique biocompatibility, nontoxicity, hydrophilicity, solubilization properties, and rapid clearance from a patient's body. In a preferred embodiment, the PEG component can be chosen from a mixture of PEGs having different average molecular weights. The inventors have found that by utilizing a mixture of more than one PEG molecular weight polymer, that better control of the properties of the resulting compositions can be attained. While the use of more the one molecular weight PEG monomer offers flexibility, it should be appreciated that there is no limit on the number of different molecular weight PEG monomers can be used. For example, the benefits of the invention may be obtained using three or more different molecular weight PEG monomers.

The hydrophobic A-blocks are utilized because of their biodegradable, biocompatible, and solubilizing properties. The in vitro and in vivo degradation of these hydrophobic, biodegradable polyester A-blocks is well understood and the degradation products are naturally occurring (or have properties that are equivalent to naturally occurring products) or biocompatible compounds that are readily metabolized and/or eliminated by the patient's body.

The concentration at which the block copolymers are soluble at temperatures below the gelation temperature may be considered as the functional concentration. Generally speaking, block copolymer concentrations of as low as 3% and up to about 50% by weight can be used and still be functional. However, concentrations in the range of about 5 to 40% are preferred and concentrations in the range of about 10-30% by weight are most preferred. In order to obtain a viable gel phase transition with the copolymer, a certain minimum concentration, e.g. 3% by weight, is required. At the lower functional concentration ranges, the formed gel will be weak and may result in phase separation. Where the polymer concentrations are higher, a more stronger gel network may be formed.

The mixture of the biodegradable copolymer and peptide/protein drugs, and/or other types of drugs, may be prepared as an aqueous solution of the copolymer below the gelation temperature to form a drug delivery liquid where the drug may be either partially or completely dissolved. When the drug is partially dissolved, or when the drug is essentially insoluble, the drug exists in a colloidal state such as a suspension or emulsion. The disclosed polymers are advantageously used in the parenteral administration such as intramusclular or subcutaneous, intratumoral, intracranial (or into the resected tumor cavity), intraarticular, ocular, topical, transdermal, vaginal, buccal, transmucosal, pulmonary, transurethral, rectal, nasal, oral, or aural administration, whereupon the polymers will undergo a reversible thermal gelation since body temperature will be above the gelation temperature.

This system will cause minimal toxicity and minimal mechanical irritation to the surrounding tissue due to the biocompatibility of the materials, pliability of the gel, and the precise control of the swelling characteristics in physiological areas where swelling would result in damage to the surrounding tissue. The polyester blocks in the system will further be completely biodegraded to caproic, lactic acid, glycolic acid, and other corresponding monomers within a specific time interval. The polyethylene glycol blocks are removed from the body by excretion. The drug release, gel strength, gelation temperature and degradation rate can be controlled by proper design and preparation of the various copolymer blocks, namely, through modifications of the weight percent of A-blocks and B-blocks, the mole percentages of caprolactone, lactate and glycolate, and the molecular weight and polydispersity of the ABA or BAB block copolymers. Drug release is also controllable through adjustment of the concentration of polymer in the drug delivery liquid.

A dosage form comprised of a solution of the block copolymer that contains either dissolved drug or drug as a suspension or emulsion is administered to the body. This formulation then spontaneously gels, due to the reverse thermal gelation properties of the block copolymer, to form a drug depot as the temperature of the formulation rises to body temperature. The only limitation as to how much drug can be loaded into the formulation is one of functionality. Namely, the drug load may be increased until the thermal gelation properties of the copolymer are adversely affected to an unacceptable degree, the drug release properties are altered adversely or until the properties of the formulation are adversely affected to such a degree as to make administration of the formulation unacceptably difficult. Generally speaking, it is anticipated that in most instances the drug will make up between about 0.01 to 20% by weight of the formulation with ranges of between about 0.01 to 10% being highly common. These ranges of drug loading are not limiting to the invention. Provided functionality is maintained, drug loadings outside of these ranges fall within the scope of the invention.

A distinct advantage to the compositions described herein lies in the ability of the block copolymer to increase the solubility of many drug substances. The combination of the hydrophobic A-block(s) and hydrophilic B-block(s) renders the block copolymer amphiphilic with distinct hydrophilic and hydrophobic domains which stabilize and solubilize hydrophobic drugs. In that regard, it functions much as a soap or surfactant in having both hydrophilic and hydrophobic properties. This is particularly advantageous in the solubilization of hydrophobic or poorly water soluble drugs such as cyclosporin and paclitaxel. What is surprising is the degree of drug solubilization of most, if not all, drugs since the major component of the block copolymer is the hydrophobic A-block content. However, as already discussed, even though the hydrophobic polymer block(s) are the major component, the block copolymer is water soluble and it has been found that there is an additional increase in drug solubility when combined in an aqueous phase of the block copolymer.

Another advantage to the compositions described herein lies in the ability of the block copolymer to increase the chemical stability of many drug substances, for example, paclitaxel. Various mechanisms for the degradation of drugs, which lead to a drug's chemical instability, have been observed to be inhibited when the drug is in the presence of the block copolymer. For example, paclitaxel is substantially stabilized in the aqueous polymer composition of the present invention relative to certain aqueous solutions of these same drugs in the presence of organic co-solvents. This stabilization effect on paclitaxel is illustrative of the effect that can be achieved with many other drug substances.

In certain situations the drug loaded polymer may be administered in the gel state instead of as a solution. The gelation may be the result of raising the temperature of a drug laden polymer solution to above the gelation temperature of the polymer prior to administration, or may be caused by raising the concentration of the polymer in the solution to above the saturation concentration at the temperature of administration, or may be caused by addition of additives to the polymer solution which causes the solution to gel. In either event, the gel thus formed may be administered in parenteral administration such as intramusclular or subcutaneous, intratumoral, intracranial (or into the resected tumor cavity), intraarticular, ocular, topical, transdermal, vaginal, buccal, transmucosal, pulmonary, transurethral, rectal, nasal, oral, or aural administration of drugs.

This invention is applicable to bioactive agents and drugs of all types including nucleic acids, hormones, anticancer-agents, and it offers an unusually effective way to deliver polypeptides and proteins. Many labile peptide and protein drugs are amenable to formulation into the block copolymers of the invention and can benefit from the reverse thermal gelation process described herein. While not specifically limited to the following, examples of pharmaceutically useful polypeptides and proteins may be erythropoietin, oxytocin, vasopressin, adrenocorticotropic hormone, epidermal growth factor, platelet-derived growth factor (PDGF), prolactin, luliberin, luteinizing hormone releasing hormone (LHRH), LHRH agonists, LHRH antagonists, growth hormone (human, porcine, bovine, etc.), growth hormone releasing factor, insulin, somatostatin, glucagon, interleukin-2 (IL-2), interferon-$\alpha$, $\beta$, or $\gamma$, gastrin, tetragastrin, pentagastrin, urogastrone, secretin, calcitonin, enkephalins, endorphins, angiotensins, thyrotropin releasing hormone (TRH), tumor necrosis factor (TNF), nerve growth factor (NGF), granulocyte-colony stimulating factor (G-CSF), granulocyte macrophage-colony stimulating factor (GM-CSF), macrophage-colony stimulating factor (M-CSF), heparinase, bone morphogenic protein (BMP), hANP, glucagon-like peptide (GLP-1), interleukin-11 (IL-11), renin, bradykinin, bacitracins, polymyxins, colistins, tyrocidine, gramicidins, cyclosporins or synthetic analogues, modifications and pharmacologically active fragments thereof, enzymes, cytokines, antibodies or vaccines.

The only limitation to the polypeptide or protein drug which may be utilized is one of functionality. In some instances, the functionality or physical stability of polypeptides and proteins can also be increased by addition of various additives to the solid powder or powder wax AB, ABA, or BAB block copolymers of the invention either before or after forming into solid form. Additives can also be added to aqueous solutions or suspensions of the polypeptide or protein drug. Additives, such as polyols (including sugars), amino acids, surfactants, polymers, other proteins and certain salts may be used in connection with stabilizing the drugs themselves without altering the properties of the drug delivery composition. These additives can be readily incorporated into the block copolymers which will remain reconstitutable with reverse thermal gelation properties.

Developments in protein engineering may provide the possibility of increasing the inherent stability of peptides or proteins. While such resultant engineered or modified proteins may be regarded as new entities in regards to regulatory implications that does not alter their suitability for use in the present invention. One of the typical examples of modification is PEGylation where the stability of the polypeptide drugs can be significantly improved by covalently conjugating water-soluble polymers, such as polyethylene glycol, with the polypeptide. Another example is the modification of the amino acid sequence in terms of the identity or location of one or more amino acid residues by terminal and/or internal addition, deletion or substitution. Any improvement in stability enables a therapeutically effective polypeptide or protein to be continuously released over a prolonged period of time following a single administration of the drug delivery liquid to a patient.

In addition to the previously listed peptide or protein based drugs, other drugs from all therapeutic and medically useful categories may be utilized. These drugs are described in such well-known literature references as the Merck Index, the Physicians Desk Reference, and The Pharmacological Basis of Therapeutics. A brief listing of specific agents is provided for illustration purposes only, and shall not be deemed as limiting: anti-cancer agents such as actinomycin D, anastrozole, azacitidine, bevacizumab, bicalutamide, bleomycin, BCNU, bortezomib, camptothecin, capecitabine, carboplatin, cetuximab, daunorubicin, dasatinib, docetaxel, doxorubicin, epirubicin, erlotinib, exemestane, gefitinib, gemcitabine, goserelin, imatinib, STI-571, irinotecan, lapatinib, letrozole, leuprolide, methotrexate, mitomycin, oxaliplatin, paclitaxel, pemetrexed, rituximab, sorafenib, sunitinib, tamoxifen, taxotere, tegafur-uracil, temozolomide, trastuzumab, triptorelin, vinorelbine; antipsychotics such as olanzapine and ziprasidone; antibacterials such as cefoxitin; anthelmintics such as ivermectin; antivirals such as acyclovir; immunosuppressants such as cyclosporin A (cyclic polypeptide-type agent), steroids, and prostaglandins. Additional anti-cancer agents include porcabazine, dacarbazine, altretamine, displatin, mercaptopurine, thioguanine, fludarabine phosphate, cladribine, pentostatin, fluorouracil, cytarabine, azacitidine, vinblastine, vincristine, etoposide, teniposide, topotecan, dactinomycin, idarubincin, plicamycin, flutamide, leuprolide, gasoerelin, aminoglutethimide, amsacrine, hydroxyurea, asparaginase, mitoxantrone, mitotane, retinoic acid derivative, bone marrow growth factors amifostine, carmustine, lomustine, semustine, anti-VEGF, etc.

In order to illustrate preferred embodiments of this invention, the synthesis of various low molecular weight ABA block copolymers of 60 to 85% by weight hydrophobic A-blocks (polyesters), and 15 to 40% by weight hydrophilic B-block (polyethylene glycol "PEG") were completed. The object was the preparation of AB, ABA or BAB block copolymers having average molecular weights of about 1500 to 10,000 with an A-block including at least 60% ε-caprolactone and another monomer and a B-block comprising a polyethylene glycol (PEG), wherein the molecular weight of the B-block is from 300 to 2000 Daltons. In the case of triblock copolymers, the polymers more preferably have a weight average molecular weight from 4000 to 8000 Daltons, and most preferably a molecular weight from 5500-7500. In the case of AB diblock polymers, the polymers more preferably have a molecular weight range from 1500-4500, and most preferably between 2000-4000. The block copolymer is a solid powder or powder wax composition that, when formed into an aqueous solution, is capable of exhibiting reverse thermal gellation. The following are examples that illustrate preferred embodiments of the invention but are intended as being representative only.

Example 1

Synthesis of PCLG-PEG-PCLG ABA Triblock Copolymer by Ring Opening Polymerization 20 g of poly(ethylene glycol) having a nominal molecular weight of 1000, which was stated to be 981 on the certificate of analysis, was dried under vacuum (≤1 mmHg) at 120° C. for 3 hours. 43.13 g of ε-caprolactone and 4.87 g of DL-lactide and/or glycolide were added to the reaction flask. When the reaction mixture temperature reached 80° C., the polymerization was initiated by the addition of 27 mg stannous octoate to the reaction mixture. The reaction mixture was heated at 155° C., for an additional eight hours. Unreacted monomers were removed by vacuum (≤1 mmHg) for 1 hour at 140° C. and the residual polymer was dissolved in water. Unreacted PEG, water soluble low molecular weight polymers and monomers were removed by precipitation of the polymer solution in hot water bath (70° C.). Excess water was removed by freeze drying to give white solid powder or wax-powder polymer. Molecular weight and compositions of the resulting block copolymer were determined by gel permeation chromatography using PEG standards and NMR, respectively.

Example 2

Synthesis of the MPEG-PCG Diblock Polymer by Ring Opening Copolymerization

Following the general procedure outlined in Example 1, the diblock copolymers were synthesized using a mixture of poly(ethylene glycol)-monomethyl ether having nominal average molecular weights of 550 and 750, and reacting the mixture with ε-caprolactone and glycolide to form an AB-block copolymer. The AB-block copolymer had a PEG average molecular weight of 590 based on the weighted average molecular weights of the PEG 550 and PEG 750 used in making the AB-block copolymer.

Example 3

Synthesis of the MPEG-PCG-PEGM BAB Triblock Copolymer

The diblock copolymer of Example 2 (25 g; 12.7 mmole) was added to 170 ml anhydrous toluene. The residual water adsorbed to the polymer was removed by azeotropic distillation to a final volume of 125 ml. HMDI (1.25 g; 6.35 mmole) and stannous octate (0.11 g: 0.27 mmole) were added to the solution, stirred at 60° C. for 10 hours and at 130° C. for 6 hours under a dry nitrogen atmosphere. The toluene in the solution was removed by distillation to final volume of 70 ml. The reaction mixture was precipitated in 300 ml of diethyl ether two times. The residual solvent was removed by drying under high vacuum at 100° C., resulting in a BAB triblock copolymer.

Example 4

Following the general procedure outlined in Examples 1-3, other AB, ABA and BAB type of block copolymers were synthesized. Composition Nos. 2, 4-5, and 11-13 were synthesized using PEG of nominal molecular weights of 550, 1000, and 1450 without combining PEG of differing molecular weight. Composition Nos. 1, 3 and 6-10 were synthesized using PEG of more than one molecular weight selected from 550, 750, 1000, and 1450. For example, polymer 1 was synthesized by combining PEG 550 with PEG 750 before carrying out a reaction similar to that described in Example 1. Similarly, Composition Nos. 3 and 6-10 were synthesized using PEG 1000 and PEG 1450 in various ratios. The PEG Mw listed in Table II below for polymers 1, 3 and 6-10 are weighted averages of the PEG polymers that were utilized in the synthesis. Table II also shows the various ε-caprolactone, DL-lactide and glycolide content in each of the block copolymers. The molecular weight values listed in Table III are approximate values due to the normal and expected variation between nominal molecular weight and the molecular weight reported on the corresponding certificate of analysis.

TABLE II

| # | Polymer type | PEG Mw | PCLG/PEG (w/w) | ε-caprolactone (mole %) | Lactide (mole %) | Glycolide (mole %) | Polymer state |
|---|---|---|---|---|---|---|---|
| 1 | AB | 590 | 2.4 | 90 | 0.0 | 10 | Solid powder |
| 2 | ABA | 1450 | 1.7 | 100 | 0.0 | 0.0 | Solid powder |
| 3 | ABA | 1309 | 2.2 | 85 | 5 | 10 | Powder-wax |
| 4 | ABA | 1000 | 2.4 | 90 | 0.0 | 10 | Powder-wax |
| 5 | ABA | 1450 | 1.7 | 90 | 10 | 0.0 | Powder-wax |
| 6 | ABA | 1216 | 2.2 | 87.5 | 0.0 | 12.5 | Powder-wax |
| 7 | ABA | 1309 | 2.0 | 90 | 0.0 | 10 | Powder-wax |
| 8 | ABA | 1309 | 2.2 | 90 | 0.0 | 10 | Powder-wax |
| 9 | ABA | 1309 | 2.2 | 92.5 | 0.0 | 7.5 | Solid powder |
| 10 | ABA | 1309 | 2.2 | 95 | 0.0 | 5 | Solid powder |
| 11 | ABA | 1450 | 2.0 | 95 | 0.0 | 5 | Solid powder |
| 12 | ABA | 1450 | 2.2 | 90 | 0.0 | 10 | Powder-wax |
| 13 | BAB | 550 | 2.1 | 95 | 0.0 | 5 | Solid powder |

Example 5

Reconstitution of Polymer

All of the synthesized block copolymers were reconstitutable and possessed reversible thermal gelation properties. 1.15 g of solid polymer and 3.85 g of water was weighed in 20 ml vial and the vial was placed in a 60° C. water bath for about 1 minute gentle mixing. The vial was vortexed for few seconds followed by mixing in a 4° C. cool room. After 20 minutes, the turbid polymer solution changed to a clear free-flowing solution. The gelation temperatures of reconstituted polymers (23%, w/w) are presented in Table III.

TABLE III

| # | Reversible thermal gelation | Gelation temperature (Tgel) | Reconstitution | Mn (by NMR) | Mw (by GPC) |
|---|---|---|---|---|---|
| 1 | Yes | 31.0 | Yes | ND | ND |
| 2 | Yes | 47.0 | Yes | ND | ND |
| 3 | Yes | 35.0 | Yes | ND | ND |
| 4 | Yes | 21.4 | Yes | 3638 | 5625 |
| 5 | Yes | 45.0 | Yes | ND | ND |
| 6 | Yes | 29.1 | Yes | 4287 | 5822 |
| 7 | Yes | 37.7 | Yes | 4303 | 5777 |
| 8 | Yes | 31.0 | Yes | ND | 6712 |
| 9 | Yes | 33.0 | Yes | 4306 | 6575 |
| 10 | Yes | 32.5 | Yes | 4254 | 6534 |
| 11 | Yes | 33.1 | Yes | 4557 | 6393 |
| 12 | Yes | 35.1 | Yes | 4875 | 7036 |
| 13 | Yes | 29.0 | Yes | ND | ND |

Example 6

Phase Diagram

Figure 1:
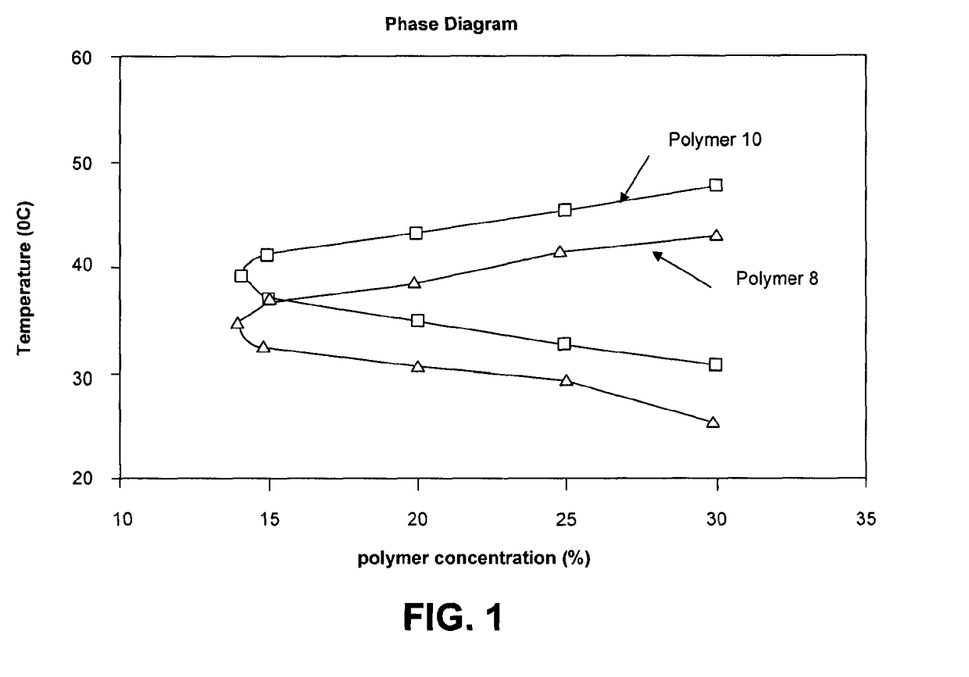
FIG. 1 is a phase diagram illustrating the effect of monomer composition on gelation behavior of aqueous solutions of block copolymer, studied at different concentrations and temperatures.
Figure 2:
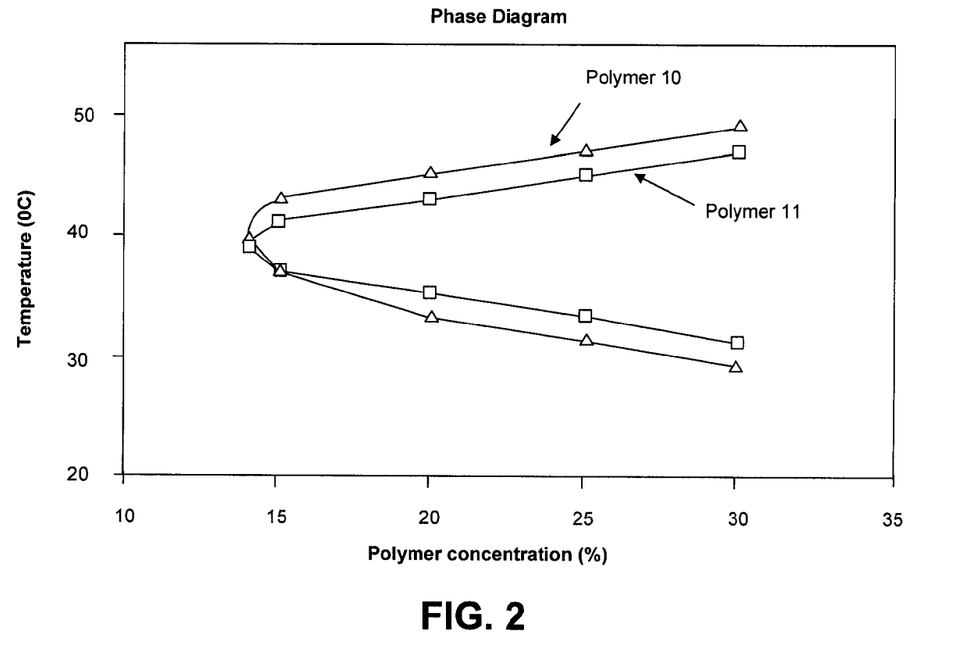
FIG. 2 is a phase diagram illustrating the effect of polymer hydrophobicity on gelation behavior of aqueous solutions of a block copolymer, studied at different concentrations and temperatures.

The thermal gelation behavior of aqueous solution of various block copolymers was studied. Following the procedure outlined in Example 5, the aqueous solutions of polymer in water (10-30% w/w) were prepared. The change in the viscosity was observed as a function of temperature ranging between 10-60° C. Results from the FIGS. 1 and 2 clearly demonstrated the effect hydrophobic composition on the thermal gelation behavior.

Example 7

Polymer Swelling Behavior

Figure 3:
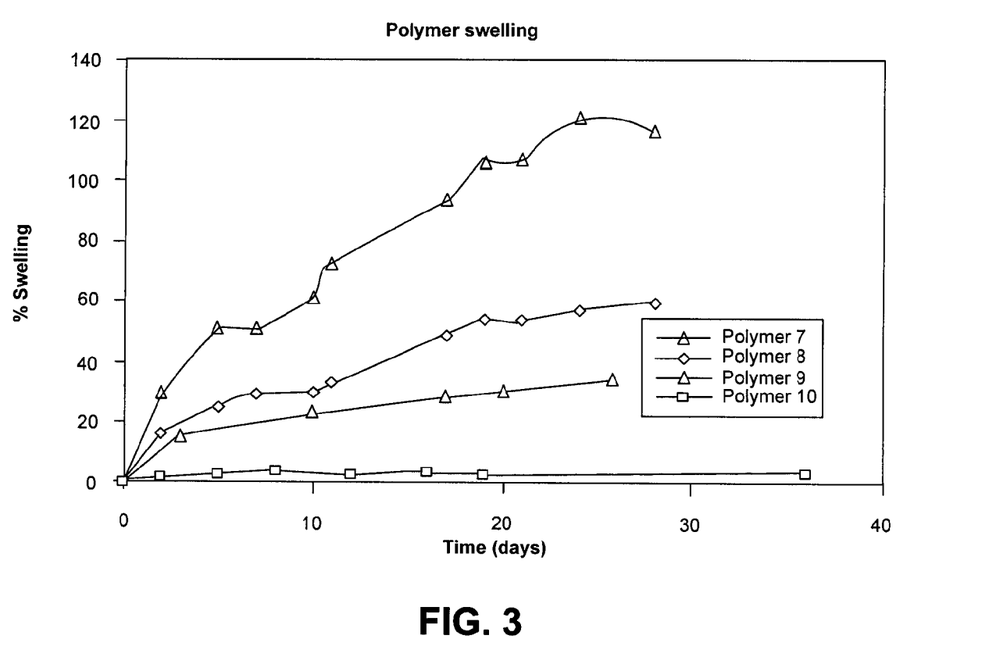
FIG. 3 is a graph illustrating the percent swelling of block copolymer thermal gel over a period of days for different block copolymer compositions.

Modulation of swelling of the block copolymer reverse thermal gelation systems was achieved by changing the hydrophobic monomer content and chain length. 23% (w/w) aqueous solutions of block copolymers 7, 8, 9, and 10 were prepared by following the procedure out lined in Example 5. 3 ml aliquots of these four polymer solutions were placed in 20 ml scintillation vials. After the gel was formed (37° C., 20 minutes), to each vial was added 5 ml of water (37° C.) and incubated in an incubator-shaker at 37° C. Periodically, the water layer was removed and weight of the gel was obtained. The water layer was replaced with fresh water and % polymer swelling was calculated. The results are presented in FIG. 3. The swelling of copolymers with the same PEG molecular weight (polymers 8, 9 and 10) depended on the hydrophobic composition of the polymer. The higher ε-caprolactone content polymer had much lower swelling than lower ε-caprolactone content polymer. When PEG molecular weight and ε-caprolactone content was the same, the polymer with a longer hydrophobic chain length had lower swelling than shorter hydrophobic chain length polymer. As shown in FIG. 3, the block copolymer composition of Composition No. 10 is capable of exhibiting less than 10% swelling after 5 days of aqueous exposure, and less than 5% swelling after 30 days of aqueous exposure.

Example 8

Solubility Enhancement of Drugs

Paclitaxel is a hydrophobic drug that is highly insoluble in water (solubility is approximately 4 μg/ml in water). However, the drug showed significantly higher solubility in aqueous solution of (ε-caprolactone-co-glycolide)-PEG-(ε-caprolactone-co-glycolide) copolymers. In a 23% w/w aqueous copolymer solution, the paclitaxel is soluble up to 12 mg/ml. The solubilization rate was much faster as compared to a previously synthesized polymer (see Rathi et al., U.S. Pat. No. 6,004,573 discussed above). For solubilization studies, the calculated amount of Paclitaxel was add to the block polymers aqueous solution (prepared according to Example 5) and stirred for 10-20 minute at room temperature or 4° C. The polymer-paclitaxel suspension was changed to clear solution in 20 minutes and could be filtered through 0.2 μm pore size filter. Solubility of paclitaxel in the filtered polymer solution was confirmed by HPLC assay. This experiment demonstrated ~3000 fold increase in solubility of paclitaxel. Similar increase in the solubility of other hydrophobic drugs has been achieved.

Example 9

Drug Release

Figure 4:
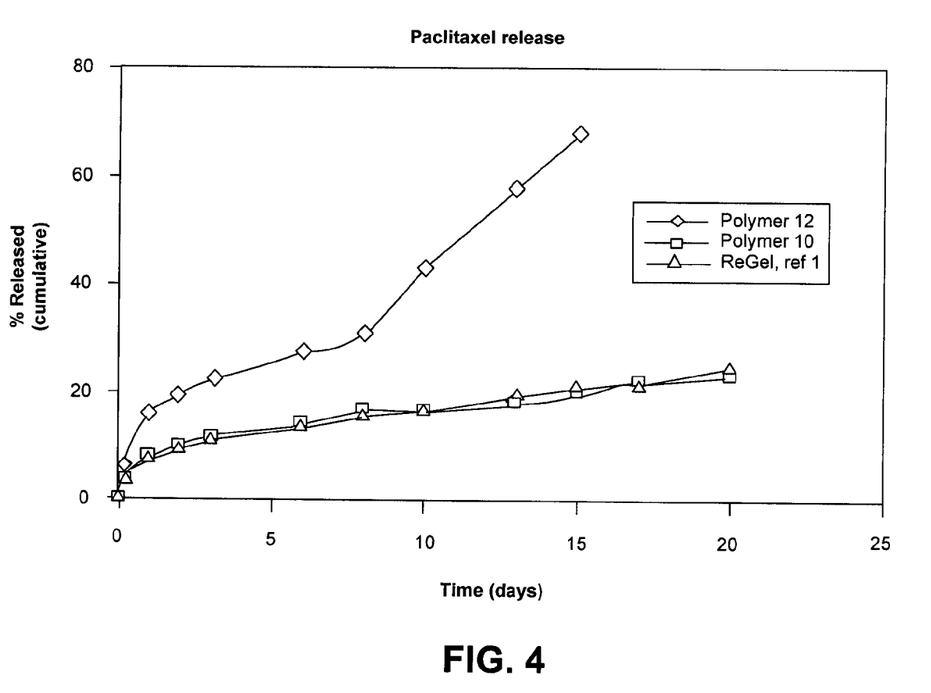
FIG. 4 is a release profile of paclitaxel from block copolymer thermal gel formulation showing the cumulative controlled release of the paclitaxel for approximately 20 days for different block copolymer compositions.

This example illustrates the drug release profile of paclitaxel (a model drug) from (ε-caprolactone-co-glycolide)-PEG-(ε-caprolactone-co-glycolide) polymer gel. Paclitaxel (30 mg) was dissolved in a 4.97 g of 23% (w/w) polymer aqueous solution, as described in Example 5. The dissolution test was performed using a modified USP-II dissolution apparatus. The release of paclitaxel was studied from a 1.0 g drug-polymer depot at 37° C. using 138 mM NaCl, 2.7 mM KCl, 0.2% (w/v) NaN$_3$, and 10 mM phosphate buffer, pH-7.4 (containing 4% (w/v) Cremophor EL and 2.4% (w/v) Tween-80) as the dissolution medium. The released paclitaxel content was analyzed by HPLC. The results are presented in FIG. 4. The ε-caprolactone content in polymer clearly demonstrated the effect on drug release while having desirable reconstitution properties. Specifically, the Composition No. 10 released between about 10 to 15% of paclitaxel in five days and 15% to 20% of paclitaxel in 20 days. As shown in FIG. 4, reconstitutable polymers of the present invention are capable of exhibiting release characteristics similar to prior drug release compositions that are not reconstitutable such as ReGel (i.e., require the application of additives or extended agitation to place in an aqueous form exhibiting reverse thermal gellation).

Stability Enhancement of Drugs

Paclitaxel is highly unstable in aqueous cosolvent solutions (e.g. in water/acetonitrile solutions). The paclitaxel contained in either 23% by weight aqueous (ε-caprolactone-co-glycolide)-PEG-(ε-caprolactone-co-glycolide) triblock copolymer solutions (i.e., below the gelation temperature of the copolymer) or gels (i.e., above the gelation temperature of the copolymer) was >90% intact after 30 days in storage (2 to 8° C. and 37° C.) whereas paclitaxel in cosolvent solution had >50% of paclitaxel degraded in less than one week at 37° C.

The above description will enable one skilled in the art to make AB, ABA or BAB type block copolymers that are solid powder or powder wax form that upon reconstitution become aqueous solutions having reverse thermal gelation properties and to utilize the same in the field of drug delivery. Although the controlled delivery of paclitaxel is illustrated in the examples to show the functionality of hydrogels formed from aqueous solutions of block copolymers, these descriptions are not intended to be an exhaustive statement of all drugs which can be utilized and loaded into the biodegradable block copolymers. Certainly, numerous other drugs from various classes of therapeutic agents are well suited for delivery from aqueous compositions of block copolymers as described herein. Neither are all block copolymers which may be prepared, and which demonstrate the critical reverse thermal gelation property, are specifically shown. However, it will be immediately apparent to one skilled in the art that various modifications may be made without departing from the scope of the invention which is limited only by the following claims and their functional equivalents.

The invention claimed is:

1. An AB-, ABA-, or BAB-block copolymer composition, said block copolymer comprising:
   at least a first AB, ABA, or BAB block copolymer component comprising a first hydrophobic A-block and a first hydrophilic B-block, wherein the first hydrophobic A-block is a biodegradable polyester comprising about 60% to 95% caprolactone by mole percent and at least one second polyester-forming monomer, and the first hydrophilic B-block has a first average molecular weight and comprises polyethylene glycol;
   at least a second AB, ABA, or BAB block copolymer component comprising a second hydrophobic A-block and a second hydrophilic B-block, wherein the second hydrophobic A-block comprises biodegradable polyester, and the second hydrophilic B-block has a second average molecular weight and comprises polyethylene glycol, wherein the second average molecular weight is different from the first average molecular weight;
   wherein the block copolymer composition has a total weight average molecular weight from 1500 to 10,000 Daltons, a total A-block content of the composition from about 60 to 85% by weight, and a total B-block content of the composition from about 15% to 40% by weight, wherein the total weight average molecular weight of the B-block in the composition is from 300 to 2000 Daltons, wherein the block copolymer composition is a powder or wax at room temperature, is capable of exhibiting reverse thermal gellation when formed as an aqueous polymer solution, and is capable of being converted into an aqueous polymer solution in less than thirty minutes by agitating without the use of additives or heat exceeding 60° C.

2. An aqueous polymer composition suitable for parenteral administration comprising the block copolymer composition of claim 1.

3. The block copolymer composition of claim 1, wherein the total A-block content of the composition ranges from 65 to 80% by weight and the total B-block content of the composition ranges from 20 to 35% by weight.

4. The block copolymer composition of claim 1, wherein the total A-block content of the composition ranges from 67 to 75% by weight and the total B-block content of the composition ranges from 25 to 33% by weight.

5. The block copolymer composition of claim 1, wherein the second polyester monomer comprises residues of at least one of D,L-lactide, D-lactide, L-lactide, D,L-lactic acid, D-lactic acid, L-lactic acid, glycolide, glycolic acid, ε-hydroxy hexonoic acid, γ-butyrolactone, γ-hydroxy butyric acid, δ-valerolactone, δ-hydroxy valeric acid, hydrooxybutyric acids, malic acid, or copolymers thereof.

6. The block copolymer composition of claim 1, wherein the second polyester monomer comprises residues from at least one of D,L-lactide, D-lactide, L-lactide, D,L-lactic acid, D-lactic acid, L-lactic acid, glycolide, glycolic acid, ε-hydroxy hexonoic acid, or copolymers thereof.

7. The block copolymer composition of claim 1, wherein the second polyester monomer comprises residues from lactide or glycolide or copolymers thereof.

8. The block copolymer composition of claim 1, wherein the biodegradable polyester of the first A-block comprises about 85% caprolactone ki mole percent.

9. The block copolymer composition of claim 1, wherein the biodegradable polyester of the first A-block comprises about 90% caprolactone by mole percent.

10. The block copolymer composition of claim 1, wherein the biodegradable polyester of the first A-block comprises about 90 to 95% caprolactone by mole percent.

11. The block copolymer composition of claim 1, wherein the total weight average molecular weight of the B-block in the composition is from 1000 to 1600 Daltons.

12. The block copolymer composition of claim 1, wherein the total average molecular weight of the B-block in the composition is from 1200 to 1500 Daltons.

13. The block copolymer composition of claim 1, wherein the total weight average molecular weight of the B-block in the composition is from 1200 to 1500 Daltons, and the biodegradable polyester of the first A-block comprises about 90 to 95% caprolactone by mole percent and 5% glycolide.

14. The block copolymer composition of claim 1, wherein the block copolymer composition is capable of exhibiting less than 10% swelling after 5 days of aqueous exposure.

15. The block copolymer composition of claim 1, wherein the block copolymer composition is capable of exhibiting less than 5% swelling after 30 days of aqueous exposure.

16. The block copolymer composition of claim 1, wherein the block copolymer composition is capable of forming said aqueous polymer solution in less than 30 minutes without exposure to additional agents or temperatures exceeding 60° C.

17. The block copolymer composition of claim 1, wherein the solid powder block copolymer composition is capable of forming said aqueous polymer solution in less than 30 minutes without exposure to additional agents or temperatures exceeding 60° C., is capable of exhibiting less than 5% swelling after 30 days of aqueous exposure, and is capable of releasing between about 10 to 15% of paclitaxel in five days and 15% to 20% of paclitaxel in 20 days.

18. The block copolymer composition of claim 1, further comprising a drug.

19. The block copolymer composition of claim 18, wherein said drug is a polypeptide or protein, nucleic acid or gene, hormone, anti-cancer or anti-cell proliferation agent.

20. The block copolymer composition of claim 19, wherein said polypeptide or protein is oxytocin, vasopressin, adrenocorticotropic hormone, epidermal growth factor, platelet-derived growth factor (PDGF), prolactin, luliberin, luteinizing hormone releasing hormone (LHRH), LHRH agonists, LHRH antagonists, growth hormone (human, porcine, bovine, etc.), growth hormone releasing factor, insulin, erythropoietin, somatostatin, glucagon, interleukin-2 (IL-2), interferon-α, β, or γ, gastrin, tetragastrin, pentagastrin, urogastrone, secretin, calcitonin, enkephalins, endorphins, angiotensins, thyrotropin releasing hormone (TRH), tumor necrosis factor (TNF), nerve growth factor (NGF), granulocyte-colony stimulating factor (G-CSF), granulocyte macrophage-colony stimulating factor (GM-CSF), macrophage-colony stimulating factor (M-CSF), heparinase, bone morphogenic protein (BMP), hANP, glucagon-like peptide (GLP-1), interleukin-11 (IL-11), renin, bradykinin, bacitracins, polymyxins, colistins, tyrocidine, gramicidins, cyclosporins and synthetic analogues, modifications and pharmacologically active fragments thereof.

21. The block copolymer composition of claim 19, wherein said polypeptide or protein is an enzyme, cytokine, antibody or vaccine.

22. The block copolymer composition of claim 19, wherein said polypeptide or protein is erythropoietin, luteinizing hormone releasing hormone (LHRH), LHRH agonists, LHRH antagonists, growth hormones, tumor necrosis factor (TNF), nerve growth factor (NGF), granulocyte-colony stimulating factor (G-CSF), granulocyte macrophage-colony stimulating factor (GM-CSF), macrophage-colony stimulating factor (M-CSF), glucagon-like peptide (GLP-1), interleukin-11 (IL-11), cyclosporins and synthetic analogues, modifications or pharmacologically active fragments thereof.

23. The block copolymer composition of claim 18, wherein said drug is paclitaxel.

24. The block copolymer composition of claim 18, wherein said drug is an anti-cancer agent.

25. The block copolymer composition of claim 18, wherein said drug is an anti-cancer agent comprising actinomycin D, anastrozole, azacitidine, bevacizumab, bicalutamide, bleomycin, BCNU, bortezomib, camptothecin, capecitabine, carboplatin, cetuximab, daunorubicin, dasatinib, docetaxel, doxorubicin, liposomal, epirubicin, erlotinib, exemestane, gefitinib, gemcitabine, goserelin, imatinib, STI-571, irinotecan, lapatinib, letrozole, leuprolide, methotrexate, mitomycin, oxaliplatin, paclitaxel, pemetrexed, rituximab, sorafenib, sunitinib, tamoxifen, taxotere, tegafur-uracil, temozolomide, trastuzumab, triptorelin, vinorelbine, porcabazine, dacarbazine, altretamine, displatin, mercaptopurine, thioguanine, fludarabine phosphate, cladribine, pentostatin, fluorouracil, cytarabine, azacitidine, vinblastine, vincristine, etoposide, teniposide, topotecan, dactinomycin, idarubincin, plicamycin, flutamide, leuprolide, gasoerelin, aminoglutethimide, amsacrine, hydroxyurea, asparaginase, mitoxantrone, mitotane, retinoic acid derivative, amifostine, carmustine, lomustine, semustine, anti-VEGF and synthetic analogues, modifications or pharmaceutically equivalents thereof.

26. The block copolymer composition of claim 18, wherein said drug is an anti-cancer agent comprising mitomycin, bleomycin, BCNU, carboplatin, doxorubicin, daunorubicin, methotrexate, paclitaxel, taxotere, actinomycin D, camptothecin, and synthetic analogues, modifications or pharmaceutically equivalents thereof.

27. The block copolymer composition of claim 18, wherein the drug content of said composition is between about 0.01 and 20% by weight.

28. The block copolymer composition of claim 27, wherein the block copolymer composition is capable of forming said aqueous polymer solution in less than 30 minutes without exposure to additional agents or temperatures exceeding 60° C., is capable of exhibiting less than 5% swelling after 30 days of aqueous exposure, and is capable of releasing between about 10 to 15% of a drug comprising paclitaxel in five days and 15% to 20% of the drug in 20 days.

29. The block copolymer composition of claim 1, wherein the first AB, ABA, or BAB block copolymer is an ABA-block copolymer, said ABA-block copolymer comprising:
 (a) about 60 to 85% by weight of a biodegradable, hydrophobic A-block comprising a biodegradable polyester,
  wherein said A-block includes about 85% to 95% caprolactone by mole percent and at least one second polyester-forming monomer; and
 (b) about 15 to 40% by weight of a biodegradable, hydrophilic B-block comprising a polyethylene glycol,
  wherein the molecular weight of the B-block is between 1000 and 1450 Daltons;
  wherein the block copolymer composition is a powder or wax at room temperature, is capable of exhibiting reverse thermal gellation when formed as an aqueous polymer solution, and is capable of being converted into an aqueous polymer solution in less than thirty minutes by agitating without the use of additives or heat exceeding 60° C.

30. The block copolymer composition of claim 29, wherein the total weight average molecular weight of the block copolymer in the composition is from 4000 to 8000 Daltons.

31. The block copolymer composition of claim 29, wherein the total weight average molecular weight of the block copolymer in the composition is from 5500 to 7500 Daltons.

32. The block copolymer composition of claim 29, wherein the total A-block content of the composition ranges from 65 to 80% by weight and the total B-block content of the composition ranges from 20 to 35% by weight.

33. The block copolymer composition of claim 29, wherein the total A-block content of the composition ranges from 67 to 75% by weight and the total B-block content of the composition ranges from 25 to 33% by weight.

34. The block copolymer composition of claim 29, wherein the block copolymer composition is capable of forming said aqueous polymer solution in less than 30 minutes without exposure to additional agents or temperatures exceeding 60° C., is capable of exhibiting less than 5% swelling after 30 days of aqueous exposure, and is capable of releasing between about 10 to 15% of paclitaxel in five days and 15% to 20% of paclitaxel in 20 days.

35. The block copolymer composition of claim 1, wherein the first AB, ABA, or BAB block copolymer is an AB-block copolymer, said AB-block copolymer comprising:
(a) about 60 to 85% by weight of a biodegradable, hydrophobic A-block comprising a biodegradable polyester, wherein said A-block includes about 85% to 95% caprolactone by mole percent and at least one second polyester-forming monomer; and
(b) about 15 to 40% by weight of a biodegradable, hydrophilic B-block comprising a polyethylene glycol, wherein the molecular weight of the B-block is between 300 and 1450 Daltons;
wherein the block copolymer composition is a powder or wax at room temperature, is capable of exhibiting reverse thermal gellation when formed as an aqueous polymer solution, and is capable of being converted into an aqueous polymer solution in less than thirty minutes by agitating without the use of additives or heat exceeding 60° C.

36. The block copolymer composition of claim 35, wherein the total weight average molecular weight of block copolymer in the composition is from 1500 to 4500 Daltons.

37. The block copolymer composition of claim 35, wherein the total weight average molecular weight of block copolymer in the composition from 2000 to 4000 Daltons.

38. The block copolymer composition of claim 1, wherein the first AB, ABA, or BAB block copolymer is a BAB-block copolymer, said BAB-block copolymer comprising:
(a) about 60 to 85% by weight of a biodegradable, hydrophobic A-block comprising a biodegradable polyester, wherein said A-block includes about 85% to 95% caprolactone by mole percent and at least one second polyester-forming monomer; and
(b) about 15 to 40% by weight of a biodegradable, hydrophilic B-block comprising a polyethylene glycol, wherein the molecular weight of the B-block is between 300 and 2000 Daltons;
wherein the block copolymer composition is a powder or wax at room temperature, is capable of exhibiting reverse thermal gellation when formed as an aqueous polymer solution, and is capable of being converted into an aqueous polymer solution in less than thirty minutes by agitating without the use of additives or heat exceeding 60° C.

39. The block copolymer composition of claim 38, wherein the total A-block content of the composition ranges from 65 to 80% by weight and the total B-block content of the composition ranges from 20 to 35% by weight.

40. The block copolymer composition of claim 38, wherein the total A-block content of the composition ranges from 67 to 75% by weight and the total B-block content of the composition ranges from 25 to 33% by weight.

41. A method for the administration of at least one drug to a warm blooded animal in a controlled release form which comprises:
(1) providing the AB-, ABA-, or BAB-block copolymer composition of claim 1;
(2) forming an aqueous solution of said powder or wax composition by combining the copolymer composition with water without exposing to heat exceeding 60° C.; and
(3) administering said copolymer composition to said warm blooded animal.

42. The aqueous polymer composition of claim 2, wherein said aqueous polymer composition comprises about 3-50% by weight of said block copolymer.

43. The aqueous polymer composition of claim 42, wherein said aqueous polymer composition comprises about 10-30% by weight of said block copolymer.

44. The aqueous polymer composition of claim 43, wherein said aqueous polymer composition comprises about 23% by weight of said block copolymer.

* * * * *

UNITED STATES PATENT AND TRADEMARK OFFICE
CERTIFICATE OF CORRECTION

Page 1 of 1

PATENT NO. : 9,155,722 B2
APPLICATION NO. : 12/886387
DATED : October 13, 2015
INVENTOR(S) : Kirk D. Fowers et al.

It is certified that error appears in the above-identified patent and that said Letters Patent is hereby corrected as shown below:

In the Claims

Claim 8, column 18, line 53.

The claim currently reads:

-- The block copolymer composition of claim 1, wherein the biodegradable polyester of the first A-block comprises about 85% caprolactone ki mole percent. --

The claim should read:

-- The block copolymer composition of claim 1, wherein the biodegradable polyester of the first A-block comprises about 85% caprolactone by mole percent. --

Signed and Sealed this
Nineteenth Day of April, 2016

Michelle K. Lee
*Director of the United States Patent and Trademark Office*